United States Patent
Zoricak et al.

(10) Patent No.: US 10,343,152 B2
(45) Date of Patent: Jul. 9, 2019

(54) CONTINUOUS ETHYLENE OLIGOMERIZATION WITH IN-SITU CATALYST PREPARATION

(71) Applicant: NOVA Chemicals (International) S.A., Fribourg (CH)

(72) Inventors: Peter Zoricak, Calgary (CA); Stephen Brown, Calgary (CA)

(73) Assignee: NOVA Chemicals (International) S.A., Fribourg (CH)

(*) Notice: Subject to any disclaimer, the term of this patent is extended or adjusted under 35 U.S.C. 154(b) by 0 days.

(21) Appl. No.: 15/101,939

(22) PCT Filed: Dec. 17, 2014

(86) PCT No.: PCT/IB2014/067039
§ 371 (c)(1),
(2) Date: Jun. 6, 2016

(87) PCT Pub. No.: WO2015/097599
PCT Pub. Date: Jul. 2, 2015

(65) Prior Publication Data
US 2016/0303551 A1 Oct. 20, 2016

Related U.S. Application Data

(63) Continuation of application No. PCT/IB2014/067039, filed on Dec. 17, 2014.

(30) Foreign Application Priority Data

Dec. 23, 2013 (CA) .................................... 2837590

(51) Int. Cl.
C07C 2/32 (2006.01)
C07C 2/36 (2006.01)
B01J 31/14 (2006.01)
B01J 31/18 (2006.01)
C07C 11/02 (2006.01)

(52) U.S. Cl.
CPC .......... B01J 31/188 (2013.01); B01J 31/143 (2013.01); C07C 2/32 (2013.01); C07C 2/36 (2013.01); B01J 2231/20 (2013.01); B01J 2531/62 (2013.01); B01J 2540/22 (2013.01); C07C 2531/14 (2013.01); C07C 2531/18 (2013.01); C07C 2531/22 (2013.01); C07C 2531/24 (2013.01)

(58) Field of Classification Search
CPC .... B01J 31/188; B01J 31/143; B01J 2540/22; B01J 2231/20; B01J 2531/62; C07C 2/36; C07C 2/32; C07C 2531/18; C07C 2531/22; C07C 2531/24; C07C 2531/14
See application file for complete search history.

(56) References Cited

U.S. PATENT DOCUMENTS

| 5,198,563 | A | 3/1993 | Reagen et al. |
| 6,800,702 | B2 | 10/2004 | Wass |
| 7,143,633 | B2 | 12/2006 | Westerberg |
| 7,964,763 | B2 | 6/2011 | Dixon et al. |
| 8,252,956 | B2 | 8/2012 | Gao et al. |
| 8,367,786 | B2 | 2/2013 | Dixon et al. |
| 8,461,406 | B2 | 6/2013 | Overett et al. |
| 2006/0173226 | A1 | 8/2006 | Blann et al. |
| 2006/0229480 | A1 | 10/2006 | Blann et al. |
| 2011/0257350 | A1* | 10/2011 | Jaber ...................... B01J 31/188 526/145 |
| 2014/0142360 | A1* | 5/2014 | Brown ...................... C07C 2/36 585/512 |

FOREIGN PATENT DOCUMENTS

| CA | 2 708 011 A1 | 12/2011 | |
| WO | 02/04119 A1 | 1/2002 | |
| WO | 2004/056478 A1 | 7/2004 | |
| WO | 2004/056479 A1 | 7/2004 | |
| WO | WO 2013116922 A1 * | 8/2013 | ............... C07C 2/32 |

OTHER PUBLICATIONS

Carter, Anthea; Cohen, Steven A.; Cooley, Neil A.; Murphy, Aden; Scutt, James and Wass, Duncan F.; High activity ethylene trimerisation catalysts based on diphosphine ligands; Copyright the Royal Society of Chemistry 2002, Received (in Cambridge, UK) Feb. 8, 2002, Accepted Mar. 11, 2002. First published as an Advance Article on the web Mar. 20, 2002, www.rsc.org/chemcomm, pp. 858-859.

* cited by examiner

*Primary Examiner* — In Suk C Bullock
*Assistant Examiner* — Ali Z Fadhel

(57) ABSTRACT

The oligomerization of ethylene using a chromium (Cr) catalyst having a phosphorus-nitrogen-phosphorus (P—N—P) ligand is known. Reactor fouling with by-product polyethylene can be severe at operating temperatures of greater than 60° C. However, the activation of such catalysts in a continuous flow reactor at low temperatures can be difficult and activity can be low. We have now discovered that highly active Cr/P—N—P catalysts may be prepared and activated in-situ (i.e. directly in the polymerization reactor) at low temperatures (from about 30 to about 45° C.) by combining the Cr; the P—N—P ligand and an aluminoxane in the process solvent in the presence of hydrogen. The use of hydrogen allows very high productivity (greater than $1 \times 10^6$ grams of ethylene conversion per gram of Cr) at low temperature. We have also observed reactor fouling rates as low as 2 to 10 parts per million of polyethylene per hour (based on total ethylene conversion) using this process.

12 Claims, No Drawings

CONTINUOUS ETHYLENE OLIGOMERIZATION WITH IN-SITU CATALYST PREPARATION

TECHNICAL FIELD

This invention relates to a continuous flow process for the oligomerization ethylene using a Cr catalyst having a bridged diphosphine ligand. The process is operated at a low temperature; produces low levels of fouling and requires the use of hydrogen to optimize activity.

BACKGROUND ART

Alpha olefins are commercially produced by the oligomerization of ethylene in the presence of a simple alkyl aluminum catalyst (in the so called "chain growth" process) or alternatively, in the presence of an organometallic nickel catalyst (in the so called Shell Higher Olefins, or "SHOP" process). Both of these processes typically produce a crude oligomer product having a broad distribution of alpha olefins with an even number of carbon atoms (i.e. butene-1, hexene-1, octene-1 etc.). The various alpha olefins in the crude oligomer product are then typically separated in a series of distillation columns. Butene-1 is generally the least valuable of these olefins as it is also produced in large quantities as a by-product in various cracking and refining processes. Hexene-1 and octene-1 often command comparatively high prices because these olefins are in high demand as comonomers for linear low density polyethylene (LLDPE).

Technology for the selective trimerization of ethylene to hexene-1 has been recently put into commercial use in response to the demand for hexene-1. The patent literature discloses catalysts which comprise a chromium source and a pyrrolide ligand as being useful for this process—see, for example, U.S. Pat. No. 5,198,563 (Reagen et al., assigned to Phillips Petroleum).

Another family of highly active trimerization catalysts is disclosed by Wass et al. in WO 02/04119 (now U.S. Pat. Nos. 7,143,633 and 6,800,702). The catalysts disclosed by Wass et al. are formed from a chromium source and a bridged diphosphine ligand and are described in further detail by Carter et al. (Chem. Comm. 2002, p 858-9). The two phosphorous (P) atoms are preferably bridged by an amine (N) bridge and hence these ligands are typically referred to as "P—N—P" ligands. As described in the Chem. Comm. paper, the most preferred P—N—P ligands are those in which each P atom is bonded to two phenyl groups and each phenyl group is substituted with an ortho-methoxy group. Hexene-1 is produced with high activity and high selectivity by these catalysts.

Similar P—N—P ligands are disclosed by Blann et al. in WO04/056478 and WO 04/056479 (now US 2006/0229480 and US 2006/0173226). However, in comparison to the ligands of Wass et al., the disphosphine/tetraphenyl ligands disclosed by Blann et al. generally do not contain polar substituents in ortho positions. The "tetraphenyl" diphosphine ligands claimed in the '480 application must not have ortho substituents (of any kind) on all four of the phenyl groups and the "tetraphenyl" diphosphine ligands claimed in '226 are characterized by having a polar substituent in a meta or para position. Both of these types of catalysts reduce the amount of hexenes produced and increase the amount of octene (in comparison to the ligands of Wass et al.) and the catalysts are generally referred to as "tetramerization catalysts".

The performance of Cr bridged diphosphine catalysts is typically temperature dependent. The prior art generally teaches preferred operating temperatures of from 50 to 150° C., especially from 60 to 90° C. Very high activities (of greater than $2 \times 10^6$ grams of product per gram of catalyst per hour) have been reported at this temperature range, particularly when cyclohexane is used as the solvent.

It will be recognized by those skilled in the art that the preparation and activation of these catalysts can be difficult. Several approaches to optimize catalyst synthesis have been reported and claimed in the patent literature.

Dixon et al. (U.S. Pat. No. 7,964,763) teach the use of an aliphatic solvent at higher temperatures (of at least 50° C.) to optimize activity.

Dixon et al. (U.S. Pat. No. 8,367,786) disclose and claim a two stage activation process in which two activators are contacted with the Cr/P—N—P catalyst components in two separate stages. One activator is preferably an aluminoxane and the other is preferably an aluminum alkyl. Comparative examples show that premixing the first and second activations and contacting the mixture with Cr/P—N—P catalyst components produces a catalyst with low activity.

Overett et al. (U.S. Pat. No. 8,461,406) disclose and claim a different type of two stage activation in which an oligomerization catalyst is initially prepared and activated in the presence of an olefin, then subsequently diluted with another liquid that is not the liquid product from the oligomerization process.

As noted above, the activity of these catalysts is temperature dependent and very high catalyst activities are observed at temperatures of from 60-90° C.

We have now discovered a convenient, low temperature method for the in-situ activation of a Cr/P—N—P catalyst system. While not wishing to be bound by theory, it is believed that the catalyst is more stable at this temperature. According to this invention, the catalyst is prepared and activated by combining the Cr, the P—N—P ligand and the activator in-situ (i.e. in the oligomerization reactor) in the presence of hydrogen at a temperature of from about 30 to about 50° C.

DISCLOSURE OF INVENTION

The present invention provides:
a method for the preparation of an activated ethylene oligomerization catalyst under continuous flow conditions, said method comprising contacting:
A) a continuous flow of a catalyst system comprising
1) a source of chromium;
2) a P—N—P ligand defined by the formula [(R$^1$)(R$^2$)—P$^1$-bridge-P$^2$(R$^3$)(R$^4$)]; wherein R$^1$, R$^2$, R$^3$ and R$^4$ are independently selected from the group consisting of hydrocarbyl and heterohydrocarbyl and said bridge is a moiety that is bonded to both phosphorus atoms;
3) an activator;
4) solvent; and
B) hydrogen;
wherein said method is completed at a temperature of from 30 to 45° C., in an oligomerization reactor and in the absence of ethylene.

Some prior art processes for the oligomerization of ethylene specifically require that the oligomerization catalyst is prepared in the presence of ethylene or another olefin. However, under the conditions of the present invention (i.e. low temperature and in the presence of hydrogen), we have discovered that this leads to severe fouling with polymer. We have observed that this problem is substantially mitigated through a "catalyst first" start-up protocol as follows:

a) in the first step: solvent, chromium, ligand, activator and hydrogen are added to the reactor (as described above) in the absence of ethylene;

b) ethylene is added afterwards; and c) the flow of all the reactor contents described (i.e. catalyst system+activator+solvent+hydrogen+ethylene) above then continues.

This "catalyst first" start-up protocol greatly reduces fouling—which is an unusual result for which we do not have a full explanation.

Thus, in summary, the activated catalyst that is prepared in the absence of ethylene is then exposed to a continuous flow of ethylene to start the oligomerization process. The process is then continued by providing continuous flow of all of the above described chromium/activator/hydrogen/ligand/ethylene materials to the reactor.

Accordingly, in another embodiment, the present invention provides a process for the oligomerization of ethylene comprising:

1) preparing an activated oligomerization catalyst according to the method described above (in the absence of ethylene); and 2) subsequently adding a continuous flow of ethylene to said activated oligomerization catalyst; and 3) continuing to provide flows of said chromium, P—N—P ligand, activator, hydrogen, and solvent to said oligomerization reactor under continuous flow oligomerization conditions.

BEST MODE FOR CARRYING OUT THE INVENTION

Part A Catalyst System

The catalyst system used in the process of the present invention must contain three essential components, namely:
(i) a source of chromium;
(ii) a diphosphine ligand; and
(iii) an activator.

Preferred forms of each of these components are discussed below.

Chromium Source

Any source of chromium that is soluble in the process solvent and which allows the oligomerization process of the present invention to proceed may be used. Preferred chromium sources include chromium trichloride; chromium (III) 2-ethylhexanoate; chromium (III) acetylacetonate and chromium carbonyl complexes such as chromium hexacarbonyl. It is preferred to use very high purity chromium compounds as these should generally be expected to minimize undesirable side reactions. For example, chromium acetylacetonate having a purity of higher than 99% is commercially available (or may be readily produced from 97% purity material—using recrystallization techniques that are well known to those skilled in the art). The present process operates at a temperature of from 30 to 50° C. We have observed that very low Cr concentrations in the reactor are optimum for this temperature—with a range of 0.1 to $3 \times 10^{-6}$ molar being suitable and from 0.3 to $0.8 \times 10^{-6}$ being optimum.

Diphosphine Ligand Used in the Oligomerization Process

In general, the ligand used in the process of this invention is defined by the formula $(R^1)(R^2)$—$P^1$-bridge-$P^2(R^3)(R^4)$ wherein $R^1$, $R^2$, $R^3$ and $R^4$ are independently selected from the group consisting of hydrocarbyl and heterohydrocarbyl and said bridge is a moiety that is bonded to both phosphorus atoms.

The term hydrocarbyl as used herein is intended to convey its conventional meaning—i.e. a moiety that contains only carbon and hydrogen atoms. The hydrocarbyl moiety may be a straight chain; it may be branched (and it will be recognized by those skilled in the art that branched groups are sometimes referred to as "substituted"); it may be saturated or contain unsaturation and it may be cyclic. Preferred hydrocarbyl groups contain from 1 to 20 carbon atoms. Aromatic groups—especially phenyl groups—are especially preferred. The phenyl may be unsubstituted (i.e. a simple $C_6H_5$ moiety) or contain substituents, particularly at an ortho (or "o") position.

Similarly, the term heterohydrocarbyl as used herein is intended to convey its conventional meaning—more particularly, a moiety that contains carbon, hydrogen and at least one heteroatom (such as O, N, R and S). The heterohydrocarbyl groups may be straight chain, branched or cyclic structures. They may be saturated or contain unsaturation. Preferred heterohydrocarbyl groups contain a total of from 2 to 20 carbon+heteroatoms (for clarity, a hypothetical group that contains 2 carbon atoms and one nitrogen atom has a total of 3 carbon+heteroatoms).

It is preferred that each of $R^1$, $R^2$, $R^3$ and $R^4$ is a phenyl group (with an optional substituent in an ortho position on one or more of the phenyl groups).

Highly preferred ligands are those in which $R^1$ to $R^4$ are independently selected from the group consisting of phenyl and o-fluorophenyl. The resulting ligands are useful for the selective tetramerization of ethylene to octene-1 with some co product hexene also being produced.

The term "bridge" as used herein with respect to the ligand refers to a moiety that is bonded to both of the phosphorus atoms in the ligand—in other words, the "bridge" forms a link between $P^1$ and $P^2$. Suitable groups for the bridge include hydrocarbyl and an inorganic moiety selected from the group consisting of $N(CH_3)$—$N(CH_3)$—, —$B(R^6)$—, —$Si(R^6)_2$—, —$P(R^6)$— or —$N(R^6)$— where $R^6$ is selected from the group consisting of hydrogen, hydrocarbyl and halogen.

It is especially preferred that the bridge is —$N(R^5)$— wherein $R^5$ is selected from the group consisting of hydrogen, alkyl, substituted alkyl, aryl, substituted aryl, aryloxy, substituted aryloxy, halogen, alkoxycarbonyl, carbonyloxy, alkoxy, aminocarbonyl, carbonylamino, dialkylamino, silyl groups or derivatives thereof and an aryl group substituted with any of these substituents. Highly preferred bridges are those in which $R^5$ is a $C_1$ to $C_{12}$ alkyl—especially isopropyl (i.e. when $R^5$ is isopropyl).

Activator (or "Co Catalyst")

The activator may be any compound that generates an active catalyst for ethylene oligomerization. Mixtures of activators may also be used. Suitable compounds include organoaluminum compounds, organoboron compounds and inorganic acids and salts, such as tetrafluoroboric acid etherate, silver tetrafluoroborate, sodium hexafluoroantimonate and the like. Suitable organoaluminium compounds include compounds of the formula AlRS, where each R is independently $C_1$-$C_{12}$ alkyl, oxygen or halide, and compounds such as $LiAlH_4$ and the like. Examples include trimethylaluminium (TMA), triethylaluminium (TEAL), tri-isobutylaluminium (TIBA), tri-n-octylaluminium, methylaluminium dichloride, ethylaluminium dichloride, dimethylaluminium chloride, diethylaluminium chloride, ethylaluminiumsesquichloride, methylaluminiumsesquichloride, and alumoxanes (also referred to as aluminoxanes). Alumoxanes are well known in the art as typically oligomeric compounds which can be prepared by the controlled addition of water to an alkylaluminium compound, for example trimethylaluminium. Such compounds can be linear, cyclic, cages or mixtures thereof. Commercially available alumoxanes are generally believed to be mixtures of linear and cyclic compounds. The cyclic alumoxanes can be represented by the formula $[R^6AlO]_S$ and the linear alumoxanes by the formula $R^7(R^8AlO)_S$ wherein s is a number from about 2 to 50, and wherein $R^6$, $R^7$, and $R^8$ represent hydrocarbyl groups, preferably $C_1$ to $C_6$ alkyl groups, for example methyl, ethyl or butyl groups. Alkylalumoxanes especially methylalumoxane (MAO) are preferred.

It will be recognized by those skilled in the art that commercially available alkylalumoxanes may contain a proportion of trialkylaluminium. For instance, some commercial MAO contains up to 35 weight % trimethylaluminium (TMA), and commercial "modified MAO" (or "MMAO") contains both TMA and TIBA. Quantities of alkylalumoxane are generally quoted herein on a molar basis of aluminium (and include such "free" trialkylaluminium).

A combination of a MAO with additional TEAL is preferred for this invention. The combined use of MAO and TEAL can provide a cost effective cocatalyst system.

In the preparation of the catalyst systems used in the present invention, the quantity of activating compound to be employed is easily determined by simple testing, for example, by the preparation of small test samples which can be used to oligimerize small quantities of ethylene and thus to determine the activity of the produced catalyst. It is generally found that the quantity employed is sufficient to provide 500 to 5000 moles of aluminium per mole of chromium. A mix of MAO and TEAL is preferred with the moles of aluminum from the MAO that are provided being about 40 to 60 mole % of the total moles of aluminum in the activator. Molar Al/Cr ratios of from 1000/1 to 3500/1 are preferred. Additional TEAL increases the total Al/Cr ratio but may actually reduce overall costs as TEAL is much less expensive than MAO. The use of a combined MAO+TEAL cocatalyst system is shown in the examples. We have also found that the overall concentration of aluminum in the reactor should be from 1000 to $3000 \times 10^{-6}$ molar.

Part B Hydrogen

The use of hydrogen is essential to the process of the present invention. In the absence of hydrogen, very low catalyst activities are observed at the temperature of the present invention. Optimum ethylene:hydrogen ratios (weight:weight in the feed) are believed to be from 150/1 to 800/1.

Part C Catalyst: Ratios and Preparation

For comparative oligomerizations at higher temperatures, the chromium and ligand may be present in almost any molar ratio in which the ligand is provided in a molar excess to the chromium. Stated alternatively: a molar equivalent of ligand and chromium provides an active catalyst and excess ligand (though not necessary) does not generally have an adverse impact upon activity at high temperature. However, the method of this invention is undertaken at a temperature of from 30 to 45° C., especially from 35 to 45° C. At this temperature, we have observed a negative impact upon catalyst activity when a molar excess of ligand (to Cr) is used. As previously noted, we believe that the method of this invention provides a catalyst that is more stable in comparison to catalysts that we prepared at higher temperatures. However, activity has been observed to be compromised with excess ligand. While not wishing to be bound by theory, we believe that "excess" ligand may be coordinated to the catalyst (at this temperature) in a manner that impairs activity. Accordingly, the optimum ligand: Cr ratio under the low temperature condition of this invention is from 0.7/1 to 1.0/1, especially from 0.75/1 to 0.85/1.

A variety of methods are known to purify solvents used to prepare the catalysts including use of molecular sieves (3A), adsorbent alumina and supported de-oxo copper catalyst. Several configurations for the purifier system are known and depend on the nature of the impurities to be removed, the purification efficiency required and the compatibility of the purifier material and the process solvent. In some configurations, the process solvent is first contacted with molecular sieves, followed by adsorbent alumina, then followed by supported de-oxo copper catalyst and finally followed by molecular sieves. In other configurations, the process solvent is first contacted with molecular sieves, followed by adsorbent alumina and finally followed by molecular sieves. In yet another configuration, the process solvent is contacted with adsorbent alumina. One preferred purifier system consists of molecular sieves, followed by adsorbent alumina and finally followed by another set of molecular sieves.

Part D Reaction Conditions (General)

Irrespective of the process conditions employed, the oligomerization is typically carried out under conditions that substantially exclude oxygen, water, and other materials that act as catalyst poisons. In addition, the reactor is preferably purged with a nonreactive gas (such as nitrogen or argon) prior to the introduction of catalyst. A purge with a solution of MAO and/or aluminum alkyl may also be employed to lower the initial level of catalyst poisons. Also, oligomerizations can be carried out in the presence of additives to control selectivity, enhance activity and reduce the amount of polymer formed in oligomerization processes.

The process of this invention requires the use of a solvent or diluent because the undesirable formation of $C_{10}^+$ oligomers has been observed to increase under continuous flow oligomerization conditions when the concentration of octene in the reactor increases. The addition of a solvent mitigates this problem. Suitable solvents include saturated $C_6$ to $C_{20}$ aliphatics (such as hexane, heptane, etc.) and saturated cycloaliphatics (such as cyclohexane or methyl cyclohexane). Unsaturated aliphatics (especially 1-olefins such as 1-hexene; 1-heptene and 1-octene) should be avoided because the use of such unsaturates has been observed to lead to the undesired formation of higher oligomers.

Mixtures of inert diluents or solvents also could be employed. The preferred solvents are aromatic hydrocarbons or saturated aliphatics such as, for example, isobutane, pentane, toluene, xylene, ethylbenzene, cumene, mesitylene, heptane, cyclohexane, methylcyclohexane, chlorobenzene, dichlorobenzene, and mixtures of aliphatics sold under the trademark Isopar®. Cyclohexane and linear $C_6$ to $C_{10}$ saturated aliphatics are especially preferred. Heptane is an especially preferred linear aliphatic because it is readily separated from the oligomers produced by this reaction using conventional distillation techniques.

The ethylene feedstock for the oligomerization may be substantially pure or may contain other olefinic impurities and/or ethane.

The feedstock is preferably treated to remove catalyst poisons (such as oxygen, water and polar species) using techniques that are well known to those skilled in the art. The technology used to treat feedstocks for polymerizations is suitable for use in the present invention and includes the molecular sieves, alumina and de-oxo catalysts described above for analogous treatment of the process solvent.

Reactor

The present invention must be conducted under continuous flow conditions using a mixed reactor.

The term "continuous flow" is meant to convey its conventional meaning—i.e. reactants are continuously added to the reactor and product is continuously withdrawn.

Similarly, the term "mixed reactor" is meant to convey its conventional meaning—i.e. a reactor that contains an agitator or mixing system. A continuously stirred tank reactor ("CSTR") is generally preferred. However, a loop reactor in which mixing is provided by a circulating pump is also suitable (and such reactors are well known to those skilled in the art and are in commercial use).

The use of a CSTR is generally preferred as it is desirable to maintain essentially homogenous reactor conditions—i.e. as will be appreciated by those skilled in the art, a well-mixed CSTR will provide homogenous reactor conditions (in contrast to a plug flow, or tubular reactor, in which the reactor conditions are typically very different at the inlet and discharge). More than one CSTR may be used.

Although a single CSTR is preferred, it is also within the scope of this invention to (optionally) use an additional tubular reactor. If the tubular reactor is employed, it would be placed downstream of the CSTR. The tubular reactor (if used) would provide some additional ethylene conversion, thereby reducing the need to recover/recycle ethylene from the discharge.

Specific Process Conditions

The process of the present invention specifically requires a solvent and typically uses a catalyst concentration of from 0.1 to $3 \times 10^{-6}$ moles of Cr per liter (micromolar).

The reactor temperature is from about 30 to about 45° C., especially from about 35 to about 45° C. In general, lower temperatures have been observed to improve selectivity (when other reaction variables are held constant).

Chromium concentrations are from 0.1 to 3 micromolar especially 0.3 to 0.8. Reactor Hold up times (HUT where HUT=reactor volume/flow to reactor) are from 40 to 180 minutes, especially 60 to 90 minutes.

Another preferred element of the present invention is the use of ethylene concentrations of 3 to 15 weight %, especially from 5 to 10 weight %.

The total operating pressure of the process is a function of ethylene concentration, hydrogen concentration, solvent choice and temperature. The use of comparatively low temperature means that a higher ethylene concentration may be achieved at a given pressure (as ethylene solubility increases at lower temperatures). Preferred operating pressures are from 2 to 20 Mega Pascals (MPa) especially from 4 to 10 MPa.

Part E Reactor Control

The control systems required for the operation of agitated reactors are well known to those skilled in the art and do not represent a novel feature of the present invention. In general, temperature, pressure and flow rate readings will provide the basis for most conventional control operations. The increase in process temperature (together with reactor flow rates and the known enthalpy of reaction) may be used to monitor ethylene conversion rates. The amount of catalyst added to the reactor may be increased to increase the ethylene conversion (or conversely, decreased to decrease ethylene conversion) within desired ranges. Thus, basic process control may be derived from simple measurements of temperature, pressure and flow rates using conventional thermocouples, pressure meters and flow meters. Advanced process control (for example, for the purpose of monitoring product selectivity or for the purpose of monitoring process fouling factors) may be undertaken by monitoring additional process parameters with more advanced instrumentation. Known/existing instrumentation that may be employed include in-line/on-line instruments such as NIR infrared, Fourier Transform Infrared (FTIR), Raman, mid-infrared, ultra violet (UV) spectrometry, gas chromatography (GC) analyzer, refractive index, on-line densitometer or viscometer. The use of NIR or GC to measure the composition of the oligomerization reactor and final product composition is especially preferred. A GC analyzer was used to measure the composition of the reactor discharge in the accompanying examples.

The measurement may be used to monitor and control the reaction to achieve the targeted stream properties including but not limited to concentration, viscosity, temperature, pressure, flows, flow ratios, density, chemical composition, phase and phase transition, degree of reaction, polymer content, selectivity.

The control method may include the use of the measurement to calculate a new control set point. The control of the process will include the use of any process control algorithms, which include, but are not limited to the use of PID, neural networks, feedback loop control, forward loop control and adaptive control.

Catalyst Deactivation, Catalyst Removal and Polymer Removal

In general, the oligomerization catalyst is preferably deactivated immediately downstream of the reactor as the product exits the reaction system. This is to prevent polymer formation and potential build up downstream of the reactor and to prevent isomerisation of the 1-olefin product to the undesired internal olefins. It is generally preferred to flash and recover unreacted ethylene before deactivation. However, the option of deactivating the reactor contents prior to flashing and recovering ethylene is also acceptable. The flashing of ethylene is endothermic and may be used as a cooling source.

In general, many polar compounds (such as water, alcohols and carboxylic acids) will deactivate the catalyst. The use of alcohols, amines and/or carboxylic acids is preferred—and combinations of these are contemplated.

The deactivator may be added to the oligomerization product stream before or after the volatile unreacted reagents/diluents and product components are separated. In the event of a runaway reaction (e.g. rapid temperature rise) the deactivator can be immediately fed to the oligomerization reactor to terminate the reaction. The deactivation system may also include a basic compound (such as sodium hydroxide) to minimize isomerization of the products (as activator conditions may facilitate the isomerization of desirable alpha olefins to undesired internal olefins).

Polymer removal (and, optionally, catalyst removal) preferably follows catalyst deactivation. Two "types" of polymer may exist, namely polymer that is dissolved in the process solvent and non-dissolved polymer that is present as a solid or "slurry".

Solid/non-dissolved polymer may be separated using one or more of the following types of equipment: centrifuge; cyclone (or hydrocyclone), a decanter equipped with a skimmer or a filter. Preferred equipment include so called "self-cleaning filters" sold under the name V-auto strainers, self-cleaning screens such as those sold by Johnson Screens Inc. of New Brighton, Minn. and centrifuges such as those sold by Alfa Laval Inc. of Richmond, Va. (including those sold under the trademark Sharples®). The Pall Filter Company also sells filters that are suitable for removing solid polymer from the liquid process stream of this invention.

Soluble polymer may be separated from the final product by two distinct operations. Firstly, low molecular weight polymer that remains soluble in the heaviest product fraction ($C_{20+}$) may be left in that fraction. This fraction will be recovered as "bottoms" from the distillation operations (described below). This solution may be used as a fuel for a power generation system.

An alternative polymer separation comprises polymer precipitation caused by the removal of the solvent from the solution, followed by recovery of the precipitated polymer using a conventional extruder. The technology required for such separation/recovery is well known to those skilled in the art of solution polymerization and is widely disclosed in the literature.

In another embodiment, the residual catalyst is treated with an additive that causes some or all of the catalyst to precipitate. The precipitated catalyst is preferably removed from the product at the same time as by-product polymer is removed (and using the same equipment). Many of the catalyst deactivators listed above will also cause catalyst precipitation. In a preferred embodiment, a solid sorbent (such as clay, silica or alumina) is added to the deactivation operation to facilitate removal of the deactivated catalyst by filtration or centrifugation.

Reactor fouling (caused by deposition of polymer and/or catalyst residue) can, if severe enough, cause the process to be shut down for cleaning. The deposits may be removed by known means, especially the use of high pressure water jets or the use of a hot solvent flush. The use of an aromatic solvent (such as chlorobenzene) for solvent flushing is generally preferred because they are good solvents for polyethylene.

Product Work Up/Distillation

In one embodiment of the present invention, the oligomerization product produced from this invention is added to a product stream from another alpha olefins manufacturing process for separation into different alpha olefins. As previously discussed, "conventional alpha olefin plants" (wherein the term includes i) those processes which produce alpha olefins by a chain growth process using an aluminum alkyl catalyst, ii) the aforementioned "SHOP" process and iii) the production of olefins from synthesis gas using the so called Lurgi process) have a series of distillation columns to separate the "crude alpha product" (i.e. a mixture of alpha olefins) into alpha olefins (such as butene-1, hexene-1 and octene-1). The mixed hexene-octene product which is preferably produced in accordance with the present invention is highly suitable for addition/mixing with a crude alpha olefin product from an existing alpha olefin plant (or a "cut" or fraction of the product from such a plant) because the mixed hexene-octene product produced in accordance with the present invention can have very low levels of internal olefins. Thus, the hexene-octene product of the present invention can be readily separated in the existing distillation columns of alpha olefin plants (without causing the large burden on the operation of these distillation columns which would otherwise exist if the present hexene-octene product stream contained large quantities of internal olefins). As used herein, the term "liquid product" is meant to refer to the oligomers produced by the process of the present invention which have from 4 to (about) 20 carbon atoms.

In another embodiment, the distillation operation for the oligomerization product is integrated with the distillation system of a solution polymerization plant (as disclosed in Canadian Patent Application No. 2,708,011, Krzywicki et al.).

It will be appreciated that the process solvent must also be separated from the liquid product. This may be done, for example, using distillation. It is highly preferred to recycle the separated solvent back to the oligomerization reactor after it has been distilled/purified.

EXAMPLES

Continuous Operation—General Conditions

A continuously stirred tank reactor (CSTR) having a nominal volume of two liters was used for these experiments.

The CSTR was fitted with external jacket for heating/cooling.

The chromium source for the catalyst was chromium tri(acetylacetonate), or $Cr(acac)_3$. The ligand was a P—N—P ligand in which the nitrogen bridging atom was substituted with an isopropyl group and each P atom was substituted with two ortho-fluoro phenyl groups. This ligand and its synthesis are known to those skilled in the art. Further details are provided in U.S. Pat. No. 8,252,956 (Gao et al.).

The cocatalyst was a combination of modified MAO (MMAO-3A) and TEAL.

MMAO-3A was purchased as a solution of methylaluminoxine (7 weight % Al in isopentane) from Akzo-Nobel.

TEAL was purchased as a 25 wt % TEAL solution in heptane from Akzo-Nobel. Catalyst, ligand and co-catalyst were added to the reactor (i.e. "in situ" catalyst formation).

The reactor was operated in a continuous manner—i.e. product was removed from the reactor during the reaction and feed (ethylene, hydrogen, solvent and catalyst) was added continuously. Ethylene and hydrogen were added to the solvent outside of the reactor and then directed to the reactor via a common feed line. Cyclohexane was used as the solvent in all examples.

Example 1

This example illustrates the need for hydrogen. Experiments 1-3 were conducted at an ethylene flow rate of 4 grams per minute and with catalyst/co-catalyst and ligand flows as shown in Table 1. The solvent was cyclohexane. The aluminum for this experiment was provided as a combination of TEAL (56 mole % of the Al) and MAO (44 mole % of the Al). Continuous flow experiments were conducted over the course of several hours for each of the three experimental conditions shown in Table 1 (i.e. to clarify: "Experiment 1" in Table 1 describes the experimental conditions that were used for a continuous oligomerization experiment that was conducted over the course of several hours).

Exceptionally low fouling rates were observed—from 2 to 11 parts per million by weight polyethylene per hour (based on the total amount of polyethylene consumed). In addition, excellent productivity (as shown in Table 1) was also observed.

A comparative experiment was conducted in the absence of hydrogen and essentially the same conditions (i.e. except for the absence of hydrogen) as experiment 1. The amount of ethylene being converted was less than 35%, which illustrates the need for hydrogen under these operating conditions.

The experiments of this example were conducted with a startup protocol that requires that the chromium+ligand+MAO+TEAL+solvent+hydrogen are first added to the reactor in the absence of ethylene. Ethylene is then added to the reactor. This startup protocol has been observed to reduce reactor fouling. In contrast, when ethylene is the first reaction component to be added to the reactor (or if it is added together with the Cr, ligand, and aluminum) then severe reactor fouling is typically observed, particularly at temperatures of 50° C. and higher.

The term "reactor fouling rate" refers to the amount of polyethylene that is deposited on the reactor internals during the oligomerization reaction. It is expressed in units of parts per million (by weight) per hour. The parts per million (by weight) is calculated by measuring the amount of polyethylene that has been deposited on the reactor and dividing it by the total amount of ethylene that is consumed during the reaction. (For clarity: the polyethylene that fouled the reactor is obtained at the end of a reaction by cleaning the reactor and weighing the amount of polyethylene that is recovered by the cleaning). The value is then divided by the number of hours that the reaction took place. The process of this invention has been observed to provide very low fouling rates—less than 1000 parts per million per hour (even less than 100 parts per million per hour and, as shown in these examples, sometimes even less than 10 ppm per hour). In contrast, prior art batch reactions (conducted at higher temperatures, without the "catalyst first" startup protocol) typically provide reactor fouling rates of 2-5 weight % per hour (i.e. 20,000 to 50,000 parts per million by weight per hour).

ethylene flow rates. It has previously been proposed that the active oligomerization catalyst has a single P—N—P ligand per atom of Cr (and accordingly, the prior art has generally taught a preference for ligand:Cr molar ratios of about 1:1). However, under the low temperature conditions of this process, we have observed higher activities when the ligand:Cr ratio is substoichiometric, especially from about 0.75:1 to 0.85:1.

The ethylene flow rate for experimental conditions 10-14 was 6 grams per minute and the ethylene flow rate for experimental conditions 15-21 was 4 grams/minute, with other flow rates/reactor concentrations as shown in Table 2. The reaction temperature was 45° C.; the solvent was cyclohexane and the TEAL/MAO ratio was also the same as Example 1. The "catalyst first" protocol (described in Example 1) was employed for all experiments and low levels of reactor fouling were observed.

Experimental conditions 10 and 11 (ligand:Cr ratios greater than 1:1) were observed to provide low productivity. The highest productivities (based on grams of $C_6+C_8+C_{10}$ per gram of Cr) were observed at low Cr concentrations, low

TABLE 1

Hydrogen

| Run # | Total H2 Flow (g/min) | Reactor [Cr] Concentration (μM) | Total Al:Cr (mol:mol) | Ligand:Cr (mol:mol) | HUT (min) | Productivity (gProduct/gCr) | C6s (wt %) | C8s (wt %) | C-10 & C-10+ (wt %) |
|---|---|---|---|---|---|---|---|---|---|
| 1 | 0.010 | 0.34 | 2012.38 | 0.78 | 131 | 8,410,256 | 22.4 | 68.4 | 9.01 |
| 2 | 0.005 | 0.36 | 2012.38 | 0.78 | 136 | 6,945,055 | 19.9 | 71.2 | 8.75 |
| 3 | 0.015 | 0.33 | 2012.38 | 0.78 | 127 | 9,641,026 | 21.4 | 69.9 | 8.45 |

$C_6$ and $C_8$ streams use both greater than 95% alpha olefin (i.e. greater than 95% 1-$C_6$ in the $C_6$s and greater than 95% 1-$C_8$ in the $C_8$s).
$C_6$ = hexene
$C_8$ = octene
$C_{10}^+$ = decene + higher
Product = wt of $C_6 + C_8 + C_{10}^+$
wt % = weight %

Example 2—Effect of [Cr] and Ligand/Cr Ratio

This example illustrates the effect of varying the ligand to chromium ratio at different chromium concentrations and ethylene flow rates (which corresponds to longer reactor HUT) and low ligand:Cr ratios. Fouling rates of between 4 and 8 ppm/hr were observed for these experiments.

TABLE 2

| Run # | Total H2 Flow (g/min) | Reactor [Cr] Concentration (μM)* | Total Al:Cr (mol:mol) | Ligand:Cr (mol:mol) | HUT (min) | Productivity (gProduct/gCr) | C6s (wt %)** | C8s (wt %)** | C-10 & C-10+ (wt %) |
|---|---|---|---|---|---|---|---|---|---|
| L:Cr Optimization | | | | | | | | | |
| L:Cr optimization at higher [Cr] | | | | | | | | | |
| 10 | 0.020 | 2.05 | 1345.69 | 1.10 | 98 | 1,410,563 | 24.4 | 68.4 | 7.07 |
| 11 | 0.020 | 2.02 | 1345.69 | 1.38 | 97 | 1,515,458 | 16.3 | 74.7 | 8.93 |
| 12 | 0.020 | 1.90 | 1345.69 | 0.83 | 91 | 1,921,237 | 18.7 | 72.0 | 9.09 |
| 13 | 0.020 | 1.86 | 1345.69 | 0.55 | 89 | 2,092,381 | 24.4 | 65.9 | 9.45 |
| 14 | 0.020 | 1.86 | 1345.69 | 0.69 | 89 | 2,081,340 | 25.0 | 64.9 | 9.85 |
| L:Cr optimization at [Cr] = ~0.65 | | | | | | | | | |
| 115 | 0.015 | 0.65 | 2012.38 | 0.55 | 123 | 5,384,615 | 30.0 | 60.4 | 9.29 |
| 16 | 0.015 | 0.65 | 2012.38 | 1.10 | 125 | 5,208,791 | 29.3 | 59.6 | 10.79 |
| 17 | 0.015 | 0.65 | 2012.38 | 0.88 | 123 | 5,428,571 | 29.9 | 59.6 | 9.77 |
| L:Cr optimization at lower [Cr] | | | | | | | | | |
| 18 | 0.015 | 0.33 | 2012.38 | 0.85 | 127 | 9,728,938 | 25.7 | 63.8 | 10.16 |
| 19 | 0.015 | 0.34 | 2012.38 | 0.57 | 131 | 8,439,560 | 23.7 | 66.4 | 9.57 |

TABLE 2-continued

| Run # | Total H2 Flow (g/min) | Reactor [Cr] Concentration (μM)* | Total Al:Cr (mol:mol) | Ligand:Cr (mol:mol) | HUT (min) | Productivity (gProduct/gCr) | C6s (wt %)** | C8s (wt %)** | C-10 & C-10+ (wt %) |
|---|---|---|---|---|---|---|---|---|---|
| 20 | 0.015 | 0.34 | 2012.38 | 0.71 | 128 | 9,260,073 | 24.4 | 66.5 | 8.62 |
| 21 | 0.010 | 0.34 | 2012.38 | 0.78 | 131 | 8,410,256 | 22.4 | 68.4 | 9.01 |

Example 3—Effect of Al Cocatalyst

This example illustrates the effect of changing the Al:Cr ratio.

The experiments of this example were conducted in a similar manner to those of example 1 with an ethylene flow rate of 4 g/minute; a temperature of 45° C.; the "catalyst first" startup protocol of example 1 and with other concentrations (for Cr, hydrogen, aluminum:Cr ratio, Cr:ligand ratio) as shown in Table 2. The TEAL/MAO mole ratio was as previously described (56 mole % TEAL; 44 mole % MAO) for experiments 30-33. For experiment 34, the relative amount of MAO was increased (to 62%—i.e. MAO/TEAL was 62/38 on a molar basis) without a meaningful change in productivity. As MAO is more expensive than TEAL, the conditions of experiments 30-33 are preferred.

In addition, the fouling rate was observed to be 6 ppm/hr for a run that utilized higher levels of TEAL compared to 13 ppm/hr for a run that utilized low levels of TEAL.

TABLE 3

| Run # | Total H2 Flow (g/min) | Reactor [Cr] Concentration (μM)* | Total Al:Cr (mol:mol) | Ligand:Cr (mol:mol) | HUT (min) | Productivity (gProduct/gCr) | C6s (wt %)** | C8s (wt %)** | C-10 & C-10+ (wt %) |
|---|---|---|---|---|---|---|---|---|---|
| Effect of Al:Cr Ratio | | | | | | | | | |
| Effect of [Al] with a 44% MMAO-3A + 56% TEAL molar split | | | | | | | | | |
| 30 | 0.015 | 0.64 | 1350.00 | 1.10 | 123 | 5,487,179 | 23.4 | 67.4 | 9.0 |
| 31 | 0.015 | 0.62 | 2025.00 | 1.10 | 118 | 6,432,234 | 31.2 | 58.5 | 9.8 |
| 32 | 0.015 | 0.61 | 2700.00 | 1.10 | 117 | 6,527,473 | 38.4 | 49.8 | 11.2 |
| Effect of [Al] and MMAO-3A/TEAL split | | | | | | | | | |
| 33 | 0.015 | 0.34 | 2013 | 0.80 | 130 | 8,688,645 | 22.8 | 69.5 | 7.52 |
| 34 | 0.015 | 0.35 | 1456 | 0.80 | 134 | 7,369,963 | 21.2 | 70.7 | 7.87 |

INDUSTRIAL APPLICABILITY

An improved process for the selective oligomerization of ethylene enables increased production run lengths by decreasing the level of reactor fouling. The oligomers that are produced by the process have a wide variety of commercial uses, particularly as comonomers in the preparation of ethylene/alpha-olefin copolymers.

The invention claimed is:

1. A method for preparing an activated ethylene oligomerization catalyst under continuous flow conditions, said method comprising introducing into an oligomerization reactor at a temperature of 30-45° C. and in the absence of ethylene:
    A) a continuous flow of a catalyst system comprising
        1) a source of chromium at a concentration of 0.1-3 micromolar (μM);
        2) a ligand defined by the formula [$(R^1)(R^2)$—$P^1$-bridge-$P^2$—$(R^3)(R^4)$]; wherein $R^1$, $R^2$, $R^3$ and $R^4$ are independently selected from the group consisting of hydrocarbyl and heterohydrocarbyl and said bridge is a moiety that is bonded to both phosphorus atoms and is selected from hydrocarbyl, —N($CH_3$)—N($CH_3$)—, —S($R^6$)—, —Si$(R^6)_2$—, —P($R^6$)—, —N($R^6$)—, and —N($R^5$)—, wherein $R^6$ is selected from hydrogen, hydrocarbyl and halogen, and wherein $R^5$ is selected from hydrogen, alkyl, substituted alkyl, aryl, substituted aryl, aryloxy, substituted aryloxy, halogen, alkoxycarbonyl, carbonyloxy, alkoxy, aminocarbonyl, carbonylamino, dialkylamino, and silyl groups;
        3) an activator; and
        4) a solvent; and
    B) hydrogen;
    wherein, when used in a subsequent oligomerization reaction, the activated ethylene oligomerization catalyst results in less fouling than an activated ethylene oligomerization catalyst where ethylene is present during the formation of the activated ethylene oligomerization catalyst.

2. The method of claim 1 wherein said source of chromium is selected from the group consisting of chromium carboxylates, chromium halides, and chromium acetylacetonate.

3. The method of claim 1 wherein said method is conducted at a chromium concentration of from 0.3 to 0.8 micromolar (μM).

4. The method of claim 1 wherein said activator comprises an aluminoxane and at least one aluminum alkyl.

5. The method of claim 4 wherein said at least one aluminum alkyl is selected from the group consisting of trimethyl aluminum, triethyl aluminum, and mixtures thereof.

6. The method of claim 1 wherein the solvent is an aliphatic solvent.

7. The method of claim 1 wherein said solvent is cyclohexane.

8. The method of claim 1 wherein each of said $R^1$, $R^2$, $R^3$ and $R^4$ is independently selected from the group consisting of phenyl and o-fluorophenyl.

9. The method of claim 1 wherein each of $R^1$, $R^2$, $R^3$ and $R^4$ is o-fluorophenyl and wherein said bridge is defined by the formula —N($R^5$)— wherein $R^5$ is a $C_1$ to $C_{12}$ alkyl.

10. A process for the continuous oligomerization of ethylene comprising:
  1) contacting ethylene with said activated oligomerization catalyst prepared according to the method of claim 1; and
  2) continuously flowing ethylene, the catalyst system, and hydrogen to said oligomerization reactor under continuous flow oligomerization conditions.

11. The process of claim 10 wherein the oligomerization conditions comprise a temperature of from about 30° C. to about 45° C. and a pressure of from 2 to 20 MPa.

12. The process of claim 11 wherein the oligomerization reactor fouling rate is less than 1000 parts per million of polyethylene, based on the total weight of ethylene consumed.

\* \* \* \* \*